United States Patent [19]

Tomic

[11] 4,296,209

[45] Oct. 20, 1981

[54] MATERIAL AS SPONGIOSACEMENT WITH EFFERVESCENT REABSORPTIVE EFFECT

[76] Inventor: Dobrivoje Tomic, Munich, Fed. Rep. of Germany

[21] Appl. No.: 133,973

[22] Filed: Mar. 26, 1980

Related U.S. Application Data

[63] Continuation of Ser. No. 961,346, Nov. 17, 1978, abandoned.

[51] Int. Cl.$^3$ .......................... C08K 3/10; C08K 3/24; C08K 5/11; C08L 33/12
[52] U.S. Cl. .............................................. 521/85; 3/1; 128/1 R; 260/42.52; 260/998.11; 521/93; 521/106; 521/123; 521/134; 521/149
[58] Field of Search ................. 260/42, 998.11, 42.52; 3/1; 128/1 R; 521/85, 93, 106, 123, 134, 149

[56] References Cited

U.S. PATENT DOCUMENTS

| | | | |
|---|---|---|---|
| 1,381,118 | 7/1921 | Gerlach | 106/122 |
| 3,172,852 | 3/1965 | Lobos | 252/5 |
| 3,789,029 | 1/1974 | Hodosh | 521/63 |
| 3,986,212 | 10/1976 | Sauer | 3/1 |

*Primary Examiner*—Allan Lieberman
*Attorney, Agent, or Firm*—Morse, Altman, Oates & Dacey

[57] ABSTRACT

A method and material for cementing solid animal tissue in situ is disclosed. Fractured and broken bones, roots of teeth, prosthetic devices and the like are cemented in place and by means of a composition which, when mixed and applied, foams to form a porous cement and cures in place having effervescent, adhesive and partially reabsorptive properties.

2 Claims, No Drawings

MATERIAL AS SPONGIOSACEMENT WITH EFFERVESCENT REABSORPTIVE EFFECT

This is a continuation of application Ser. No. 961,346 filed on Nov. 17, 1978 and now abandoned.

The discovery involves a material as Spongiosacement with effervescent and reabsorptive effect for the purpose of cementation and coalescence of/with human or animal solid tissue, which, in addition to its use in replacement or cementing of sections of bones or roots of teeth, can also be applied in the fastening and incorporation of foreign bodies, especially in surgical procedures.

As materials compatible for bone replacement and seating of foreign bodies some so-called bone cements have long been known ("Die Knochenzemente," Enke Verlag Stuttgart). Their attachment in the bone is made possible by mechanically produced retention and there exists only sporadic surface contact between the bone and the bone tissue. Following solidification there develops a closed, smooth surface, which remains constant.

All known bone cements, however, involve numerous disadvantages, especially concerning the fixing and coalescence with surrounding tissue. As a result of their solidification, much healthy bone substance is destroyed, in spite of the fact that contact and attachment on adjacent sections of bone are achieved only sporadically. Known bone cements do not make possible an integration of adjacent tissue with the bone cement, a condition of some disadvantage concerning stability and permanence in the bone. The purpose of the discovery is that of providing a material in the form of Spongiosacement having effervescent, adhesive and partially reabsorptive properties which, upon application, combine with bone tissue quickly and totally, while producing spongisoa-like areas for ossification and penetration in hard and soft tissue, and also possessing reabsorptive substances for this purpose and this process, so that both the immediate stability and complete integration of the material and its optimal incorporation in the organism are accomplished.

The discovery rests on the knowledge that the problem here stated is resolvable by means of a compound based on an effervescent substance having a comparative admixture of reabsorptive substance.

The object of the discovery is a basic carbonaceous material in the form of Spongiosacement which, in addition to a PMMA powder, contains an appropriate effervescent, reabsorptive and/or porous substance identifiable by its creation of a condition of cementation and incorporation in both the bone sections and the material as a result of moistening and silafication produced by acid or other caustic and adhesive action.

Because of the uncomplicated composition of the patentable effervescent Spongiosacement and because of the gentle and controllable effervescent effect and reabsorbability of admixed substances, application of the patentable material in both plastic and solid form is possible. The process of effervescence is initiated by the action of acid upon the material and its extent depends on concentration or proportion of active substances. The applied PMMA remains the constant medium and framework. As a result of the effect of phosphoric acid on the patentable Spongiosacement an immediate effervescence of $CaCO_3$ and release of $CO_2$ occurs, through which simultaneously spongiosa-like surfaces develop.

The process within the bones also leads simultaneously to cauterization and abrasion or formation of adhesive surfaces, producing total meshing and joining throughout.

This process of incorporation is then continued in approximately 8 weeks as a result of penetration and coalescence of tissue in the lagoons and porous areas, whereby upon admixture of a reabsorbable substance such as $Na_2HPO_4$ or others additional free openings develop to allow penetration of tissue. When the patentable effervescent-reabsorptive Spongiosacement is applied in this way, optimal integration and incorporation are achieved in the organism or bone tissue. The patentable material can be applied in plastic or solid form, and variable amounts of effervescent $CaCO_3$ and reabsorptive $Na_2HPO_4$ substance with PMMA serve as basic formulation, as well as the caustic or acid medium in concentrated degrees.

A compound of the powder in Spongiosacement, of the type noted below is especially advantageous, particularly when applied in the jawbone or as replacement for roots of teeth. Experimentation and success related to surgery of the jaw suggest there is a strong possibility of applying the effervescent-reabsorptive Spongiosacement in orthopedics, emergency surgery following accidents, and other areas as well.

Production of this patentable material entails the incorporation and mixing of individual components in the way which is usual and customary in the pharmaceutical industry. Production of the powder begins appropriately with the familiar PMMA-powder already mentioned. With this are incorporated the required components, $CaCO_3$ and $Na_2HPO_4$ in appropriately pre-mixed form. The familiar liquid substance of the selected PMMA powder is applied as monomer. The patentable material in the stated form is suitable as an independent implant, replacement for solid tissue, for attaching and cementing solid tissues one to another and/or with other foreign bodies, as well as a substance for stratification. In addition to the advantages already mentioned, the patentable Spongiosacement offers the advantage that, for example, the contact surfaces of an implant are substantially increased, a matter of great importance concerning function and stress.

The following example is intended as a detailed description of the discovery.

EXAMPLE

This example illustrates the preferred composition of the patentable compound in the form of a powder mixture to be combined with a monomer, as stated above.

| Components | Approximate Content | Approximate Content in % |
|---|---|---|
| PMMA | 7,0 g | 70 |
| $CaCO_3$ | 2,0 g | 20 |
| $Na_2HPO_4 \cdot 12H_2O$ | 1,0 g | 10 |

I claim:

1. A cement mixture for use in surgical and therapeutic procedures in animals, comprising
   (a) approximately 70% by weight polymethylmethacrylate as a cementitious substance,
   (b) approximately 20% $CaCO_3$ as effervescent medium,
   (c) approximately 10% $Na_2HPO_4 \cdot 12H_2O$ as reabsorptive substance, and, (d) phosphoric acid as an agent for activating said medium to cause said medium to effervesce whereby when said cement is mixed and applied to an animal bone, solid tissue and the like the effervescent effect and reabsorptive substance will produce voids in said cement prior to the curing of said cement in situ.

2. The method of cementing bones, teeth and prosthetic devices in an animal, comprising the local application in said animal of an uncured mixture by weight of approximately 70% PMMA, approximately 20% $CaCO_3$, approximately 10% $Na_2HPO_4.12H_2O$ mixed with a monomeric liquid and phosphoric acid and allowing said mixture to cure in situ.

* * * * *